(12) United States Patent
Schultheis et al.

(10) Patent No.: US 11,510,553 B2
(45) Date of Patent: Nov. 29, 2022

(54) LIGHT GUIDE OR IMAGE GUIDE COMPONENTS FOR DISPOSABLE ENDOSCOPES

(71) Applicant: SCHOTT AG, Mainz (DE)

(72) Inventors: Bernd Schultheis, Schwabenheim (DE); Björn Bleisinger, Riesweiler (DE); Andreas Dietrich, Guldental (DE); Markus Kappel, Roxheim (DE); Hubertus Russert, Jugenheim (DE); Martin Cramer, Wiesbaden (DE); Thomas Weingärtner, Gau-Algesheim (DE)

(73) Assignee: SCHOTT AG, Mainz (DE)

( * ) Notice: Subject to any disclaimer, the term of this patent is extended or adjusted under 35 U.S.C. 154(b) by 55 days.

(21) Appl. No.: 17/037,402

(22) Filed: Sep. 29, 2020

(65) Prior Publication Data

US 2021/0022588 A1 Jan. 28, 2021

Related U.S. Application Data

(63) Continuation of application No. PCT/EP2019/057616, filed on Mar. 26, 2019.

(30) Foreign Application Priority Data

Mar. 29, 2018 (DE) ..................... 10 2018 107 523.5

(51) Int. Cl.
*A61B 1/00* (2006.01)
*B29C 45/14* (2006.01)
(Continued)

(52) U.S. Cl.
CPC ........ *A61B 1/00126* (2013.01); *A61B 1/0011* (2013.01); *A61B 1/0017* (2013.01);
(Continued)

(58) Field of Classification Search
CPC .............. A61B 1/00126; A61B 1/0011; A61B 1/00117; A61B 1/0017; B29C 45/14426;
(Continued)

(56) References Cited

U.S. PATENT DOCUMENTS 3,581,738 A 6/1971 Moore
4,783,135 A 11/1988 Utsumi
(Continued)

FOREIGN PATENT DOCUMENTS

DE 1596485 7/1970
DE 3724749 2/1988
(Continued)

OTHER PUBLICATIONS

Hewak, "Fiber and guided wave optics—Fabrication of Optical Fiber", Encyclopedia of Modern Optics 2005, Abstract.
(Continued)

*Primary Examiner* — Mary Ellen Bowman
(74) *Attorney, Agent, or Firm* — Ruggiero McAllister & McMahon LLC

(57) ABSTRACT

The disclosure relates to diagnostic, surgical, and/or therapeutic devices for being introduced into the human or animal body or for in vitro examination of human or animal blood samples or other body cells, in particular to an endoscope or a disposable endoscope that includes at least one illumination light guide and/or image guide for transmitting electromagnetic radiation, the illumination light guide or image guide having a proximal end face for incoupling or outcoupling of electromagnetic radiation and a distal end face for incoupling or outcoupling of electromagnetic radiation. The proximal and/or distal end faces consist of plastic elements that are transparent at least partially or in sections thereof, the transparent plastic being biocompatible and/or having non-toxic properties to human or animal cell cultures for
(Continued)

exposure durations of less than one day. This allows for the production of assemblies for disposable endoscopes, inter alia.

27 Claims, 5 Drawing Sheets

(51) Int. Cl.
| | |
|---|---|
| *B29D 11/00* | (2006.01) |
| *F21V 8/00* | (2006.01) |
| *G02B 6/06* | (2006.01) |
| *G02B 6/36* | (2006.01) |

(52) U.S. Cl.
CPC .... *A61B 1/00117* (2013.01); *B29C 45/14426* (2013.01); *B29D 11/00663* (2013.01); *G02B 6/0006* (2013.01); *G02B 6/0008* (2013.01); *G02B 6/06* (2013.01); *G02B 6/3624* (2013.01); *B29K 2995/0026* (2013.01)

(58) Field of Classification Search
CPC ............ B29D 11/00663; G02B 6/0006; G02B 6/0008; G02B 6/06; G02B 6/3624; B29K 2995/0026
See application file for complete search history.

(56) References Cited

U.S. PATENT DOCUMENTS

| | | | |
|---|---|---|---|
| 4,807,597 | A | 2/1989 | Tsuno |
| 4,867,529 | A | 9/1989 | Utsumi |
| 4,964,710 | A | 10/1990 | Leiner |
| 5,436,655 | A | 7/1995 | Hiyama |
| 5,704,899 | A | 1/1998 | Milo |
| 5,761,356 | A | 6/1998 | Li |
| 6,249,348 | B1 | 6/2001 | Jung |
| 6,398,721 | B1 | 6/2002 | Nakamura |
| 6,556,851 | B1 | 4/2003 | Ott |
| 10,393,957 | B1 | 8/2019 | Potter |
| 11,215,752 | B1 | 1/2022 | Lin |
| 2004/0246744 | A1 | 12/2004 | Krupa |
| 2005/0197623 | A1 | 9/2005 | Leeflang |
| 2006/0041193 | A1 | 2/2006 | Wright |
| 2006/0069314 | A1 | 3/2006 | Farr |
| 2006/0072893 | A1 | 4/2006 | Wied |
| 2006/0152926 | A1 | 7/2006 | Hama |
| 2006/0279950 | A1 | 12/2006 | Hama |
| 2007/0249907 | A1 | 10/2007 | Boulais |
| 2008/0013900 | A1 | 1/2008 | Harris |
| 2008/0142828 | A1 | 6/2008 | Yang |
| 2008/0300456 | A1 | 12/2008 | Irion |
| 2009/0163342 | A1 | 6/2009 | Kolberg |
| 2009/0312607 | A1 | 12/2009 | Sunagawa |
| 2009/0321348 | A1 | 12/2009 | Hoermann |
| 2010/0010314 | A1 | 1/2010 | Krattiger |
| 2011/0182552 | A1* | 7/2011 | Russert ................... G02B 6/40 |
| | | | 29/428 |
| 2011/0282160 | A1 | 11/2011 | Bhadri |
| 2012/0010465 | A1 | 1/2012 | Erikawa |
| 2012/0289779 | A1 | 11/2012 | Kinoshita |
| 2013/0175720 | A1 | 7/2013 | Otsuka |
| 2013/0342110 | A1 | 12/2013 | Yamamoto |
| 2014/0107630 | A1 | 4/2014 | Yeik |
| 2014/0221749 | A1 | 8/2014 | Grant |
| 2014/0303551 | A1 | 10/2014 | Germain |
| 2014/0350343 | A1 | 11/2014 | Kim |
| 2014/0376868 | A1 | 12/2014 | Ritter |
| 2015/0016140 | A1 | 1/2015 | Weingrtner |
| 2015/0049994 | A1 | 2/2015 | Schultheis |
| 2015/0216418 | A1 | 8/2015 | Ammon |
| 2015/0374217 | A1 | 12/2015 | Sinofsky |
| 2016/0022119 | A1 | 1/2016 | Shahmoon |
| 2016/0227985 | A1 | 8/2016 | Ikeda |
| 2016/0334616 | A1 | 11/2016 | Vayser |
| 2017/0003164 | A1 | 1/2017 | Tanaka |
| 2017/0052319 | A1* | 2/2017 | Schultheis ............... G02B 6/32 |
| 2017/0231698 | A1 | 8/2017 | Goldfarb |
| 2018/0055342 | A1 | 3/2018 | Sakai |
| 2018/0228354 | A1 | 8/2018 | Yabe |
| 2019/0014979 | A1 | 1/2019 | Czupalla |
| 2019/0270667 | A1 | 9/2019 | Sumita |
| 2019/0290100 | A1 | 9/2019 | Ramachandran |
| 2019/0346649 | A1 | 11/2019 | Tanaka |
| 2019/0374095 | A1 | 12/2019 | Lord |
| 2020/0178781 | A1 | 6/2020 | Tabata |
| 2020/0222712 | A1 | 7/2020 | Schultheis |
| 2020/0253592 | A1 | 8/2020 | Popejoy |
| 2020/0301064 | A1 | 9/2020 | Kojima |
| 2021/0022588 | A1 | 1/2021 | Schultheis |
| 2021/0093170 | A1 | 4/2021 | Schultheis |
| 2021/0145257 | A1 | 5/2021 | Levinson |
| 2021/0282631 | A1 | 9/2021 | Schultheis |

FOREIGN PATENT DOCUMENTS

| | | |
|---|---|---|
| DE | 69720736 | 3/2004 |
| DE | 102004048741 | 5/2006 |
| DE | 102006053487 | 5/2008 |
| DE | 102006040214 | 7/2008 |
| DE | 102007026234 | 12/2008 |
| DE | 102008044938 | 3/2010 |
| DE | 102009004159 | 7/2010 |
| DE | 102011114575 | 4/2013 |
| DE | 102012100233 | 5/2014 |
| DE | 102013208838 | 3/2015 |
| DE | 102011119972 | 10/2015 |
| DE | 102014208756 | 11/2015 |
| DE | 102015015041 | 5/2017 |
| DE | 102017108698 | 10/2018 |
| DE | 102017122756 | 4/2019 |
| DE | 102018107523 | 10/2019 |
| DE | 102019125912 | 4/2021 |
| EP | 1890173 | 2/2008 |
| EP | 2072477 | 3/2010 |
| EP | 3097845 | 11/2016 |
| GB | 1242883 | 8/1971 |
| JP | S61143120 | 9/1986 |
| JP | S63151918 | 6/1988 |
| JP | H10258022 | 9/1998 |
| JP | 2000079089 | 3/2000 |
| JP | 2002531846 | 9/2002 |
| JP | 2003290135 | 10/2003 |
| JP | 2009018081 | 1/2009 |
| JP | 2015228887 | 12/2015 |
| JP | 2017524505 | 8/2017 |
| JP | 2017195960 | 11/2017 |
| WO | 8912479 | 12/1989 |
| WO | 2013092498 | 6/2013 |
| WO | 2016185537 | 11/2016 |

OTHER PUBLICATIONS

EN 60601-1, 3rd edition, table 3.
European Medical Device Directive MDD 93/42 EEC.
DIN EN ISO 10993, Fifth Edition, Aug. 2018.
Regulation (EU) 2017/745 of Apr. 5, 2017.
English translation of DIN EN ISO 10993-1: Apr. 2010.
English translation of Written Opinion dated Jul. 4, 2019 for corresponding International Application PCT/EP2019/057616,4 pages.
English translation of International Preliminary Report on Patentability dated Sep. 29, 2020 for corresponding International Application PCT/EP2019/057616, 5 pages.
International Search Report dated Jul. 4, 2019 for corresponding International Application PCT/EP2019/057616, with English translation, 6 pages.

(56) References Cited

OTHER PUBLICATIONS

DIN EN ISO 10993-5, "Biological evaluation of medical devices—Part 5: Tests for in vitro cytotoxicity (ISO 10993-5:2009) English version of DIN EN ISO 10993-5:2009-10", Oct. 2009, 44 pages.

* cited by examiner

LIGHT GUIDE OR IMAGE GUIDE COMPONENTS FOR DISPOSABLE ENDOSCOPES

CROSS-REFERENCE TO RELATED APPLICATIONS

The present application is a continuation of international patent application no. PCT/EP2019/057616, filed on Mar. 26, 2019, which in turn claims the benefit of German Patent Application No. 10 2018 107 523.5, filed on Mar. 29, 2018, each of which is incorporated herein by reference.

BACKGROUND OF THE DISCLOSURE

1. Field of the Disclosure

The present disclosure relates to a diagnostic, surgical, and/or therapeutic device for being introduced into the human or animal body or for in-vitro examination of human or animal blood samples or other body cells. In particular, the present disclosure related to an endoscope or disposable endoscope that comprises at least one illumination light guide and/or image guide for transmitting electromagnetic radiation, which illumination light guide or image guide has a proximal end face for incoupling and/or outcoupling of electromagnetic radiation and a distal end face for incoupling and/or outcoupling of electromagnetic radiation.

2. Discussion of the Related Art

Endoscopes for diagnosis, for minimally invasive interventions, or for therapy are known to have rigid or flexible designs and have been sufficiently described in the literature. Nowadays, disposable endoscopes are increasingly being used, in particular to increase patient safety during medical examinations, therapies and/or minimally invasive interventions, since single use allows to prevent contamination. In fact, prior art endoscopes have been designed so as to be reprocessable in terms of medical technology, i.e. they can be cleaned, sterilized and, above all, they are autoclavable.

Nevertheless, it may occasionally happen, due to incorrect application of reprocessing or unfavorable design of such devices, that the necessary reduction in the number of microbes fails to be achieved and hence microbes may be transferred to the patient during the next application. This can be prevented by using such disposable endoscopes.

Another aspect for the increased use of disposable endoscopes is economic assessment. In particular the reprocessing process that has to be carried out properly and regularly after each treatment implies high costs for the practicing doctor or the clinic nowadays. Moreover, high investments are required for purifying devices such as thermal disinfectors and autoclave devices and/or plasma sterilization devices, so that, overall, the use of such disposable endoscopes is justified.

Another advantage results from the fact that such disposable endoscopes can be used as transportable hand-held devices and can therefore also be employed in emergency medicine, in military emergency missions or in regions that are difficult to access, for example during disaster relief missions, where in particular reprocessing options are not available.

Such disposable endoscopes, also known as single-use endoscopes, as described in the literature have been described in the following documents, for example:

Document U.S. Pat. No. 3,581,738 A1 is directed to a disposable endoscope comprising a body of synthetic resinous material having a generally tubular side wall defining a speculum and a unitary elongated light-conducting member embedded in the side wall, the member being formed of a light-conducting material clad with a transparent material having an index of refraction different from that of the light-conducting material, the body being formed of two mating halves divided axially of the endoscope, each half having a member-enclosing element.

Document U.S. Pat. No. 4,964,710 A1 is directed to a rigid endoscope equipped with an objective lens system, an ocular lens and an intermediate relay lens. The relay system is a hybrid system that uses both plastic and glass components. The plastic components comprise an even number (N) of axially aligned lenses, each having a length which is of the order of their diameter. The plastic lenses comprise an odd number (N minus 1) of axially aligned plano glass cylinders with polished end faces.

Document EP 1890173 A1 is directed to a method for producing an optical light guide that can be used in such endoscopes. A plurality of optical fibers are bundled, and the fiber bundle is cut at a part of a mouthpiece which is fixed to an intermediate part of the fiber bundle. Thus, the fiber bundle is divided into a first optical fiber bundle and a second optical fiber bundle. Division surfaces of the first and second optical fiber bundles have the same properties and conditions since the first and second optical fiber bundles are formed of the fiber bundle that is obtained by bundling the same optical fibers. The first optical fiber bundle is assembled in an insertion section of an endoscope and the second optical fiber bundle is assembled in a flexible tube, whereby a first light guide is formed in the insertion section of the endoscope and a second light guide is formed in the flexible tube. Thereby, a separable light transmission path of the light guide is formed.

Since such endoscopes are subject to high cost pressure due to their single use, the assemblies and components have to be producible in a cost-effective way. Among the main components for imaging and illumination are light guides or image guides. These are currently still assembled and processed in rather complex processing steps. What makes the current illumination light guides or image guides comparatively expensive is often due to complex mechanical components partly combined with optical elements such as lenses that form part of such light guides or image guides, and sometimes complex processing steps such as grinding and polishing of the end faces are moreover involved.

On the other hand, particular lighting requirements must also be taken into account when using endoscopes, especially in medical technology. In addition to transmitting the light provided by a light source to the examination site in the best possible loss-free manner, this includes a true-to-color or an intentionally colored representation of the examination site and also the avoiding of introducing unnecessary heat to the examination site.

If active electronic components are used, such as camera chips and/or LEDs for lighting, it is moreover necessary to take into account requirements with regard to electrical insulation, electrical shielding and patient leakage currents, which must not exceed maximum threshold values, depending on the field of application of the endoscope. For applications at the heart, for example, a maximum leakage current of 10 µA is required, corresponding to CF classification (see EN 60601-1, $3^{rd}$ edition, tab. 3).

In addition to these illumination-related and electrical requirements, requirements regarding biocompatibility must also be observed. For biocompatibility, it is necessary to ensure that the material is compatible with the human organism. For medical devices that might come into contact with the human body, regulatory requirements request to determine and assess possible interactions and undesirable side effects. The selection of the required tests depends on the type of contact and duration of contact in the human body. According to European Medical Device Directive MDD 93/42 EEC, this biological assessment of a product is always necessary if there is direct contact between the material or product and the patient.

The main standards for biological tests and evaluation of materials are DIN EN ISO 10993 and the test according to United States Pharmacopeia Class VI (USP Class VI). Although the much more extensive ISO 10993 was originally intended to replace the test according to USP Class VI, the USP test is used very frequently today in particular for evaluating biocompatible plastics. For this purpose, the materials intended for invasive application are evaluated with regard to their chemical compounds on the one hand, and are on the other hand subjected to a cytotoxicity test in which possible toxic effects to living cell cultures are examined. The requirements for this are summarized in DIN EN ISO 10993, especially in parts -1 and -5 (DIN EN ISO 10993-1: 2010-04). In the United States, this is subject to FDA requirements. The requirements corresponding to DIN EN ISO 10993 are specified in USP Class VI there.

Another advantage of the endoscopes in the form of single-use endoscopes is that they do not require to take into account the known reprocessing methods in the form of cleaning or disinfection processes involving strongly basic solutions and sterilization by autoclaving at temperatures of up to 135° C. and typical steam pressures of about 3 bar, which in particular permits to choose more cost-effective materials. Only RoHS (Restriction of Hazardous Substances) and REACH (Registration, Evaluation, Authorization and Restriction of Chemicals) regulations have to be considered for the materials.

Therefore, an object of the present disclosure is to provide illumination light guides or image guides for disposable endoscopes or assemblies comprising illumination light guides, image guides, and/or cameras, which are particularly cost-effective in manufacture while meeting typical lighting requirements for endoscopes in medical technology, in particular high transmittance, and providing for good color reproduction. This should come in combination with high biocompatibility and low cytotoxicity in compliance with the medical requirements and effects.

SUMMARY OF THE DISCLOSURE

The object of the disclosure is achieved by having the proximal and/or distal end faces made of transparent plastic elements at least partially or in sections thereof or having a transparent plastic overmolded thereto. The transparent plastic is biocompatible and/or has non-toxic properties to human or animal cell cultures for exposure durations of less than one day. This allows for the production of illumination light guides or image guides in a very cost-effective way, while otherwise complex end processing such as grinding and polishing of the proximal or distal end faces can be dispensed with. The biocompatibility and the non-toxic properties of the plastics provide for invasive intervention in the body (in vivo) or enable in-vitro examinations on cell cultures or blood samples without damaging or altering them.

By appropriately choosing the plastic, it is possible to provide high-quality optical systems that meet the lighting requirements for endoscopes, especially since in the case of disposable endoscopes the temperature resistance of the plastic can in particular be lower, providing for a less limited choice. Suitable plastics include polymers from at least one of the material classes of cyclo-olefin copolymers, polycarbonates, polyethylene terephthalates, perfluoroalkoxy polymers, polyvinylidene fluorides, polymethyl methacrylates, polymethyl methacrylimides, acrylic-styrene-acrylonitrile copolymers, or room temperature crosslinking silicone, hot crosslinking liquid silicones, epoxy casting resins or adhesives, thermally or UV crosslinking acrylate casting resins, polyurethane casting resins, polyester casting resins, or mixtures and/or combinations thereof. Care must be taken to choose respective biocompatible variants that meet the requirements of the standards mentioned in the introductory part. In this respect, particularly suitable materials are thermoplastics which are easily injection molded and which are transparent, e.g. PC, PMMA, COC, etc., but also plastics that can be applied as casting resin and which permit to achieve respective smooth surfaces with a very low roughness value. Moreover, the plastics mentioned above are available in a biocompatible version.

In particular for mechanical connection to other components of the endoscope, it may be contemplated that the proximal and/or the distal end faces additionally have a respective mechanical interface in the form of a ferrule contour which is made of plastic or injection molded from plastic to the illumination light guide or image guide, and this plastic may differ from the transparent plastic of the proximal or distal end faces at least partially or in sections thereof in terms of its material, transparency, and/or color. For example, collars or shoulders and also undercut areas can be produced in this way, which allow the illumination light guide or image guide to be coupled with a handpiece and/or a shaft of the endoscope. Also, snap-in connections can be implemented in that way, inter alia, which provide for quick assembly, which in turn contributes to reducing manufacturing costs.

In particularly preferred embodiment variants, the transparent plastic of the proximal and/or distal end faces has a typical surface roughness $R_a$ of ≤1.0 μm, preferably ≤0.5 μm, most preferably ≤0.1 μm. This permits to minimize scattering losses on the surface, which would otherwise lead to a reduction in illuminance in the case of illumination light guides. With image guides, a sharp image of the illuminated object can be obtained in this way.

If the transparent plastic of the proximal or distal end faces has a refractive index which substantially matches that of the fibers or fiber components used in the core material of the illumination light guide or image guide, this permits to minimize reflection losses, which results in an increase in illuminance in the case of illumination light guides and suppresses artifacts caused by reflections in the case of image guides. Good results can already be achieved if the difference between the refractive indices of the fibers or fiber components and the clear transparent plastic is not greater than ±0.1. With a deviation of at most ±0.05, the refractive indices are already almost perfectly matched so that reflection losses in the illumination light guides are neglectable. In the case of image guides, this eliminates ghosting caused by multiple reflections.

In an advantageous embodiment of the disclosure, the illumination light guides and/or image guides for endoscopes comprise fiber bundles made up of glass optical fibers, quartz optical fibers or plastic optical fibers. Glass optical fibers are particularly suitable for the transmission of light or image information in the visible spectral range up to the near IR range. This also applies to plastic fibers, although the application length of plastic fibers is typically limited to a few centimeters up to about max. 1 m. Quartz fibers are used in particular when the application wavelength extends into the IR range up to typically 2.2 µm or when light components in the near UV range below about 400 nm are to be used. This is of particular interest in fluorescence applications. It is particularly advantageous if the bundles or individual fibers are at least partially or section-wise enclosed by a jacket, tube, shrink tube, or netting tube or if they are protected by a shaft of the endoscope. This increases the mechanical robustness of the system.

It may be contemplated that the jacket is made of a further plastic material and is in the form of an extruded cable. Such cables can be produced particularly cost-effectively in a continuous process.

It is in particular possible to use inexpensive, less temperature-stable plastics for both the cable and the ferrules in the aforementioned embodiment variants, since the single-use applications do not require thermal and/or chemical preparation processes such as autoclaving (typically @130-140° C. in saturated water vapor) and/or thermal disinfection processes (up to 95° C., purification agent with pH 11). What is usually employed for the sterilization of disposable instruments is ethylene oxide fumigation or partly plasma-based gas sterilizations (STERAD, with hydrogen peroxide and plasma; or STERIS, only with hydrogen peroxide), which are conducted at no more than 60° C.

The plastic for the extruded jacket may comprise a plastic that is translucent, opaque, or colored at least partially or in sections thereof. This allows, for example, to provide lateral illumination on the endoscope using a side-emitting optical fiber.

If the illumination light guide or image guide comprises flexible or semi-flexible fiber bundles and the jacket comprises a sheath that is rigid at least partially or in sections thereof, a shaft for a rigid endoscope can be implemented in this way.

The present disclosure further relates to rigid fiber-optic light or image guides, for example in the form of drawn fiber rods or in the form of pressed fiber rods, which advantageously are based on the same glass systems that are used for corresponding flexible glass fiber bundles. Here again, optical elements and/or ferrules can be formed cost-effectively by directly overmolding the proximal and/or distal ends of the light guide with a plastic cap.

It is particularly advantageous if the glass fibers, fiber rods or pressed fiber rods consist of a Pb-free or heavy metal-free core glass and cladding glass. Such fiber systems in particular provide high transmittance in the VIS spectral range and, owing to the comparatively high transmittance in the blue spectral range, exhibit high color fidelity, which is particularly important for the medical assessment of tissue. Often only slight differences in color of the tissue decide whether it is a benign or malignant tissue change. It is therefore important to have a high CRI value for the overall system comprising the light source, illumination light guide and imaging device, with CRI (Color Rendering Index) being a key figure of a photometric parameter that describes the quality of color rendering of light sources having the same correlated color temperature. With the glass fibers, fiber rods, or pressed fiber rods described above, a CRI value of >90 can be achieved. Such fiber systems are known from the present applicant under the name SCHOTT PURAVIS® and have been described with regard to their compositions in DE 102012100233 B4 and DE 102013208838 B4. Similar fiber systems which are likewise Pb-free are furthermore described in EP 2072477 B1.

In particular for use in endoscopes it is advantageous if glass fibers, fiber rods, or pressed fiber rods are made of a glass system which has an acceptance angle $2\alpha$ of greater than 80°, most preferably greater than 100° for the light to be transmitted. What can be achieved thereby on the one hand is that in particular light from LEDs, which usually have a very wide emission angle, can be injected into the glass fibers or fiber rods or pressed fiber rods without elevated coupling losses without the need for complex optics at the proximal end. On the other hand, wide-angle illumination can be achieved on the distal side without additionally required optics, which is most preferably for endoscopic examinations. This allows to achieve optimal illumination over the currently common camera viewing angles (usually 120° diagonally).

In a most preferred embodiment, it is contemplated that the distal and/or proximal end faces with the mechanical interface are in the form of a ferrule. The ferrule is produced separately and is fixed on the fiber bundle end or fiber rod end of the illumination light guide or image guide using an adhesive. The adhesive is in the form of a thermally curing or UV light curing adhesive which has an optical refractive index substantially matching that of the core material of the fibers or fiber components used in the illumination light guide or image guide, with a deviation thereto of not more than ±0.1, preferably not more than ±0.05, and that the refractive index of the ferrule is slightly lower than that of the adhesive. This permits to achieve high coupling efficiencies. A slightly lower refractive index of the sleeve compared to that of the adhesive helps to minimize radiation losses through the lateral side of the sleeve. Such sleeves can be produced cost-effectively as an injection molded part, here in particular as a precision injection molded part. The complete functionality with regard to accommodating the fibers, providing a mechanical interface, and defining the proximal and distal end faces in terms of their topography can be implemented in the injection molding tool. By using thermally curing or UV light curing adhesives, short processing times of about typically less than 60 s can be achieved for the assembly, i.e. glue-bonding the fiber components, which can furthermore reduce manufacturing costs.

According to a particularly advantageous embodiment, it is contemplated that the ferrule has receptacle areas for accommodating fiber bundles, which receptacle areas comprise an initially conical portion transitioning into a portion that has essentially parallel side walls, and that the ferrule furthermore has seats for electronic components, and that these receptacle areas at least partially surround the seat for electronic components. In this way, arrangements of fibers and electronic components can be implemented in which, for example, an electronic component is surrounded by a proximal or distal end face. Furthermore, substantially U-shaped arrangements are conceivable, or arrangements in which the electronic component is flanked by two opposite D-shaped distal or proximal end faces. Furthermore, 3- or 4-part distal or proximal end faces are conceivable, surrounding the electronic component in the form of circular or oval or kidney-shaped exit faces. The complete functionality of fixing and aligning the fibers and arranging the end faces can be integrated in the technical design of the ferrule and implemented in the tool design. Because of the very small dimensions, precision injection molding tools or machines are particularly advantageous here.

In an alternative embodiment, it is contemplated that the distal and/or proximal end faces with the mechanical interface in the form of a ferrule is injection molded onto cable sections previously cut to length, and that this process can be implemented as a two-stage process comprising a first step in which the cable end is fixed at least at two opposite points by tools adapted to the outer contour of the cable, and is overmolded at least partially or in sections thereof with a first plastic, and a second step in which the ferrule geometry is molded thereto using a second plastic, and that the distal and/or proximal end faces can be molded using the clear transparent plastic in any one of these steps. A two-stage process allows to prevent the fibers from fanning out in an uncontrolled manner during the injection molding process which usually involves pressures of many tens of bars. At least a kind of firm collar can be produced around the cable at the end of the cable section in the first process step, which prevents fanning out. Even opaque or colored plastics may be used as the plastics for this purpose. In the second step, the actual proximal and/or distal end faces are then produced using the clear transparent plastic.

A particularly cost-effective process which is particularly advantageous for large volumes is a continuous process in which a double contour ferrule is overmolded on a previously extruded cable at specific intervals corresponding to the length of the final component to form a mechanical interface which can then be severed in a next process step, and the proximal and/or distal end faces can be molded to the so produced cable sections by one or more further injection molding processes using clear transparent plastic. This permits to implement almost fully automated production, which in particular allows to provide such light guides in a very cost-effective way.

In another alternative embodiment, it is contemplated that a previously extruded cable is divided at specific intervals corresponding to the length of the final component, or a respective fiber bundle section is enclosed by a tube or shrink tube, and the fiber bundles disposed inside of the extruded cable section or fiber bundle section are offset inwards and the space between the end of the fiber bundle and the edge of the jacket or edge of the tube or shrink tube is filled with a clear transparent self-leveling plastic. In particular, casting resins are suitable to form light entry and exit faces having a sufficiently smooth surface in this way.

Alternatively, it may be contemplated that a previously extruded cable is divided at specific intervals corresponding to the length of the final component, or a respective fiber bundle section is enclosed by a tube or shrink tube, and that the cable jacket, the tube or shrink tube is elongated relative to the fiber bundle and the resulting cavity is filled with optically transparent plastic, or a prefabricated clear transparent plastic part or a light guide rod or fiber rod made of glass or plastic is inserted and fixed in that cavity. This is another option to provide respective light entry and exit surfaces.

In one embodiment variant, it may be contemplated that the jacket section, tube or shrink tube section defining the cavity is deformed and forms a specific light entry or light exit contour once the plastic has been cured or once the plastic part or light guide rod has been inserted. This may be done using special tools. This permits to produce different proximal and/or distal contours that may be used, for example, to hold a camera chip or to accommodate an operating channel at the distal end.

With regard to a cost-effective and also space-saving optical fiber design, it is particularly advantageous if active electronic components in the form of LEDs, sensors, or camera chips can be integrated into the molded ferrules or can be fitted thereto through a snap-in connection. For example, LED elements can be integrated in the proximal end sleeve in this way, thereby providing for a particularly high coupling efficiency, which is particularly noticeable in the illuminance at the distal end of the light guide. Besides white light LEDs, RGBW LEDs may also be used as the LEDs, which enable to switch between different colors. In addition to normal examination of tissue, this provides for particular diagnostic examinations in which the tissue is examined under specific wavelengths. Also conceivable is a combination of white light or RGBW LEDs with LEDs that emit in the deep blue spectral range (e.g. @ 405 nm) or in the near UV range. This even allows for fluorescence excitation. With regard to heat management, it may be contemplated that the LEDs are thermally coupled to heat sinks in the handpiece of the endoscope via metallic pins. The integration of a camera chip in the distal end ferrule (chip on tip) allows to directly image the tissue surface to be examined.

It may be advantageous if the proximal and/or distal end faces are in the form of an optical element to achieve specific beam shaping and therefore have a planar or convex or concave surface or a free-form surface of any desired topography. For example, with suitably designed tools, the proximal ferrule can be formed so as to comprise condenser lenses for better injection of light, for example in order to bundle the light of the usually wide emitting LEDs for in coupling it into the fibers according to the numerical aperture thereof (between 0.55 and 0.70; e.g. SCHOTT PURAVIS® GOF70 having a numerical aperture of 0.57, SCHOTT PURAVIS® GOF85 having a numerical aperture of 0.68). A respective convex lens formed on the distal end may likewise be used advantageously, for example in order to provide imaging optics for the camera chip. Furthermore, optical elements formed in this way on the distal end of the light guide can provide for a wide-angle emission characteristic such as a spherical or ring-shaped emission characteristic. A spherical emission characteristic allows for homogeneous illumination of body cavities, for example.

In a preferred embodiment, additional glass or plastic components are provided on the proximal or distal end faces for covering the active electronic components. This allows to achieve additional electrical insulation and/or shielding, which in particular enables to address applications with elevated insulation or leakage current requirements.

Furthermore, it may be contemplated for the distal ferrule comprising the camera chip to be formed as a two-component injection-molded part, with the section accommodating the camera chip made of black-colored or opaque plastic material and the distal end face made of a transparent plastic material. In this way, additional shielding of the camera chip from stray light may be achieved.

In conjunction with disposable endoscopes for medical technology, it may be particularly advantageous if so-called hybrid cables are used, through which electrical conductors can be routed in addition to optical light guiding and/or image guiding elements, in a single cable. This allows, for example, to power camera chips and to transfer image information to an evaluation unit.

In one embodiment, the extruded cable for the illumination light guide or image guide may be in the form of a multi-lumen cable that has different cavities which allows to separately route a fiber bundle, individual quartz fibers, media in the form of gases or liquids in a fluid passage, and/or electrical lines. A particular advantage thereof is the separable, independent integration of light transmitting and power-carrying components, thus providing for high functionality in very restricted space. For example, the fiber bundles can be used to guide light, quartz fibers can be used to transmit laser beam energy, for example. The electrical lines can be used to forward image signals from the camera chip to a monitor. Such multi-lumen cables can be produced very cost-effectively using appropriate extrusion tools.

The multi-lumen cable may define a flexible portion of the endoscope, or the multi-lumen cable may be made of a plastic material that is rigid at room temperature and defines a rigid shaft of the endoscope. This allows to provide particularly cost-effective flexible or rigid disposable endoscopes.

If the multi-lumen cable is formed in a co-extrusion process such that segments thereof are formed so as to selectively be transparent or opaque, this even allows to perform lighting or optical detection tasks, for example. The multi-lumen cable may be made of electrically conductive materials at least partially or in sections thereof, also within individual lumens, for example of corresponding filled plastics, and/or may be enclosed by electrically conductive materials.

All of the examples given above are suitable for providing respective inexpensive fiber-optic components or assemblies that can be installed in flexible or rigid disposable endoscopes. Here, the umbrella term 'disposable endoscopes' is meant to encompass any medical devices that can be used to direct light into the interior of the body on the one hand and on the other hand to output image information to the surgeon via optics, image guides, or camera chips. This includes angioscopes for vascular examinations with flexible endoscopes, laparoscopes for examinations in the abdominal cavity, and arthroscopes for examinations of joints with rigid endoscopes, as well as ear endoscopes, rhino endoscopes, sinuscopes, or nasopharyngoscopes, each one with a rigid endoscope, for ENT examinations.

In this case, the embodiment variants of the illumination light guides and/or image guides as described above can be integrated in a handpiece of the endoscope and may in part directly define a flexible portion or a shaft of the endoscope, depending on the design of the endoscope. With the elimination of sometimes very complex grinding and polishing processes and due to the simplified assembly, costs can be saved.

A further application option, in particular for the illumination light guide as described above in the various embodiment variants, besides their use in the field of medical devices, is their use for in-vitro diagnostic devices. For this purpose, such light guides may also be used as detector light guides. For example, a large number of such illumination or detector light guides are often used in a single device for parallel tests on blood samples, for example. In particular, the cost advantages should be mentioned here, be it as a result of a reduction in assembly costs or due to the integration of additional functions. A biocompatible version of the plastics can be directly exploited in this case, for example in order to bring blood samples or cell cultures into direct contact with the illumination or detector light guides. Furthermore, the glass or quartz optical fibers described above enable spectroscopic examinations and/or examinations using fluorescence excitation, due to their advantages in optical transmission.

Other application examples inter alia include: illumination light guides in household appliances (cooktops, dishwashing machines, refrigerators, freezer cabinets, cooking ovens, and the like) or in small kitchen appliances (blenders, toasters, table-top cooking devices, coffee machines, and the like), for example for indicating operating conditions and/or for illuminating cooking chambers or interiors, especially if they come into contact with food; home ambience lighting; and exterior/interior automotive lighting.

BRIEF DESCRIPTION OF THE FIGURES

FIG. 7 is a schematic sectional view of a distal sleeve comprising an arrangement according to FIG. 6a.

DETAILED DESCRIPTION OF THE DISCLOSURE

Figure 1:
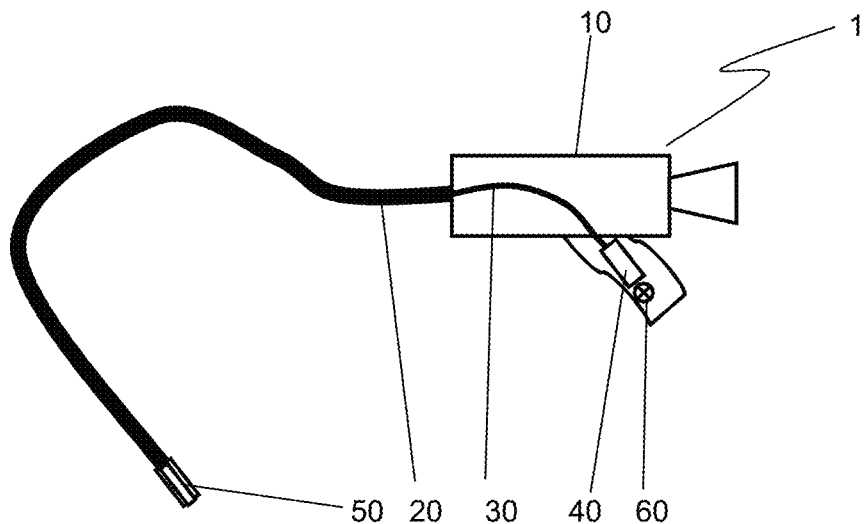
FIG. 1 is a schematic diagram of a disposable endoscope in the form of a flexible endoscope.

FIG. 1 schematically shows the configuration of an endoscope 1 according to the present disclosure. A simple flexible endoscope 1 is shown here in a highly simplified manner, by way of example, which comprises a handpiece 10 and a flexible section 20, the flexible section 20 being insertable into a body cavity, for example. What is schematically shown here is an illumination light guide 30 which has a proximal ferrule 40 adjacent to an illuminating device in the form of an LED 60 in the handpiece 10 and a distal ferrule 50 at the end of the flexible section 20. The light from LED 60 is injected at the end face of proximal ferrule 40 and transmitted through the illumination light guide 30 to the distal ferrule 50, and can then be emitted into the interior of the body through appropriate outcoupling optics. FIG. 1 does not show the imaging components, which may include C-MOS cameras, for example, which are integrated in the distal ferrule 50 and which electrically transmit the image information to a monitor (not shown). Another option are fiber-optic image guides that transmit the image information to a camera or directly to an eyepiece lens. Such image guides consist of several thousands of fine individual glass fibers only a few microns in thickness, which transmit the image information pixel by pixel.

Depending on the type and application of the endoscope, the following typical dimensions are conceivable for such light guides: length between 100 mm and 3000 mm, typically 500 to 1000 mm, light guide diameter between 0.5 mm and 5 mm, typically between 1 and 2 mm.

Figure 2:
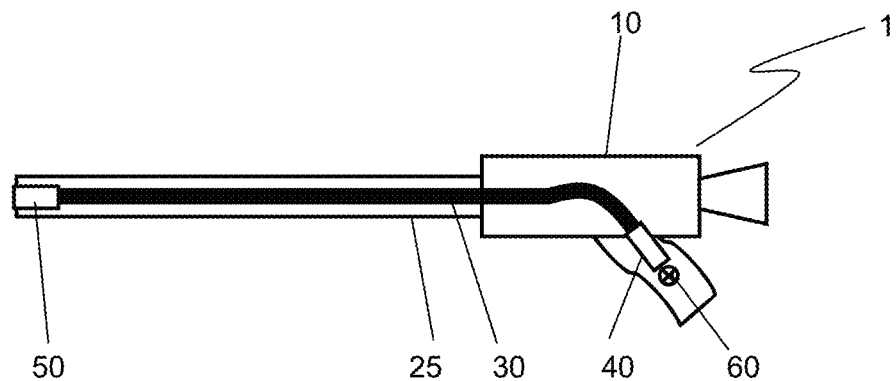
FIG. 2 is a diagram of a disposable endoscope in the form of a rigid endoscope.

FIG. 2 schematically shows an endoscope 1 in the form of a rigid endoscope 1, again in a highly simplified manner. The illumination light guide 30 is routed inside a rigid shaft 25. The imaging or image-transmitting components as mentioned above are again not shown here, for the sake of clarity.

The exemplary embodiments or manufacturing methods that will in particular be described below mainly relate to illumination light guides 30, but and can generally be transferred to image guides as well.

Figure 3:
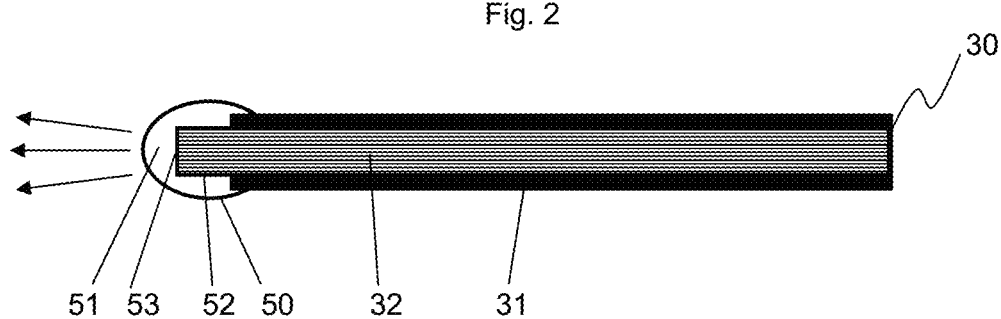
FIG. 3 is a schematic view of an illumination light guide with an adhesively bonded distal ferrule.

FIG. 3 is a fractional view of an illumination light guide 30 with a distal ferrule 50. Here, the illumination light guide 30 comprises an extruded cable 31 consisting of a plastic jacket that encloses a fiber bundle 32.

In this case, the fiber bundle is terminated by stripping the jacket from an end portion of the extruded cable 31 and fitting onto the exposed fiber bundle 32 a clear transparent ferrule that has previously been produced in an injection molding process, as a distal ferrule 50 having a receptacle area 52, and fixing the ferrule using a clear transparent resin previously introduced into this ferrule, for example in the form of a preferably quickly hot-curing or UV-curing adhesive. Thus, the distal end face 53 of the fiber bundle 32 is covered by a clear transparent plastic. This type of termination can also be applied for the proximal ferrule 40 of the illumination light guide 30. In this case, the proximal end face 43 can be covered by a clear transparent plastic.

The proximal and distal ferrules 40, 50 may additionally have mechanical interfaces 44, 54 defined by the outer contour of the proximal and distal ferrules 40, 50. These may include circumferential grooves, locking lugs, notches, flanges and the like.

Other than with a planar end face, these ferrules may also be designed as optical elements 51 in the form of lenses (convex or concave) or may have an irregular end face for beam shaping purposes. FIG. 3 shows, merely schematically, the distal ferrule 50 comprising an optical element 51 in the form of a lens tip formed in the injection molding process, which is useful to converge the exiting light, for example. The functionality of the incoupling and/or outcoupling ferrule, i.e. proximal and/or distal ferrule 40, 50 may be implemented in the design of the tool in a particularly cost-effective manner and allows the proximal or distal end faces 43, 53 to be terminated in an extremely cost-effective manner.

The fiber bundle 32 of the illumination light guide 30 or of the image guide may comprise glass optical fibers (GOF), quartz optical fibers, or plastic optical fibers (POF) enclosed by an extruded jacket as shown in FIG. 3, or by a tube or netting tube. The plastic of the jacket of the extruded cable 31 is made of an opaque colored plastic. In a further embodiment, the fiber bundle 32 itself and/or the individual fibers thereof may have an electrically conductive coating at least partially or in sections thereof, and/or the plastic of the jacket may be made at least partially or in sections thereof from or using an electrically conductive material.

The table below gives a material overview of plastics which are suitable for the jacket of the cable 31 and for the clear transparent cover of the proximal and distal end faces 43, 53 and for the proximal and distal ferrules 40, 50, respectively.

Thermoplastic elastomers (TPE) are classified into groups as follows:
TPE-A or TPA=thermoplastic copolyamides
TPE-E or TPC=thermoplastic polyester elastomers/thermoplastic co-polyesters
TPE-O or TPO=thermoplastic elastomers based on olefins, mainly PP/EPDM
TPE-S or TPS=styrene block copolymers (SBS, SEBS, SEPS, SEEPS, and MBS)
TPE-U or TPU=thermoplastic elastomers based on urethane
TPE-V or TPV=thermoplastic vulcanizates or cross-linked thermoplastic elastomers based on olefins, mainly PP/EPDM.

| Material designation | Type | Basic plastic | Particularly suitable for cable jacket | Particularly suitable for proximal/ distal end faces | Permanent temperature resistance >130° C. | Short-term temperature resistance up to 130° C. (a few hours) | Cost classification from inexpensive ($) to very expensive ($$$) (jacket material) |
|---|---|---|---|---|---|---|---|
| Cyclo-olefin copolymer | COC | transparent | | X | | | |
| Ethylene tetrafluoroethylene copolymer | ETFE | transparent | X | | X | | $$$ |
| Fluoroethylene propylene | FEP | transparent | X | | X | | $$$ |
| Polycarbonate | PC | transparent | | X | | | $ |
| Polyethylene | PE | transparent | X | | | | $ |
| Polyethylene terephthalate | PET | transparent | | X | | | |
| Perfluoroalkoxy polymers | PFA | transparent | | X | X | | $$$ |
| Polymethyl methacrylate | PMMA | transparent | | X | | | |
| Polymethyl methacrylimide, Acrylic | PMMI | transparent | | X | | | |
| Polypropylene | PP | transparent | X | | | | $ |
| Polyvinyl chloride | PVC | transparent | X | | | | $ |
| Polyvinylidene fluoride | PVDF | transparent | X | | X | | $$$ |
| Styrene-ethylene-butylene block polymers (see TPE-S) | SAN | transparent | | X | | | $ |
| Styrene-ethylene-butylene-styrene block polymers (see TPE-S) | SEBS | slightly translucent | X | | | | $ |
| Styrene-ethylene-butylene block polymers (see TPE-S) | SEB | slightly translucent | X | | | | $ |
| Tetrafluoroethylene-hexafluoropropylene-vinylidene fluoride | THV | transparent | X | | | | $$$ |

-continued

| Material designation | Type | Basic plastic | Particularly suitable for cable jacket | Particularly suitable for proximal/distal end faces | Permanent temperature resistance >130° C. | Short-term temperature resistance up to 130° C. (a few hours) | Cost classification from inexpensive ($) to very expensive ($$$) (jacket material) |
|---|---|---|---|---|---|---|---|
| Thermoplastic co-polyamides | TPE-A | transparent | X | | | X | $$ |
| Thermoplastic elastomers | TPE-E | transparent | X | | | | $$ |
| Styrene block copolymers | TPE-S | transparent | X | | | | $ |
| Thermoplastic vulcanizates or cross-linked thermoplastic elastomers based on olefins, mainly PP/EPDM, or vulcanized (cross-linked) PP/EPDM compounds | TPE-V | beige | X | | | X | $$ |
| Thermoplastic polyurethane | TPU | transparent | X | | | | $$ |
| Silicone (hot cross-linking) | HT silicone | transparent | X | | X | | $$ |
| Silicone (cross-linking @ room temperature) | RT silicone | transparent/ translucent | | X | X | | $$ |
| Liquid Silicone Rubber (thermally, condensation crosslinking or UV curing) | LSR | transparent | X | X | X | | $$$ |
| Epoxy casting resins or adhesives | | transparent | | X | partially | | $/$$ |
| Acrylic casting resins or adhesives (thermally or UV curing) | | transparent | | X | | | $ |
| Polyurethane casting resins or adhesives | | transparent | | X | | | $ |
| Polyester casting resins or adhesives | | transparent | | X | | | $ |

Especially the plastic types TPE-E, TPE-V, and TPE-U are particularly interesting for extrusion, since they exhibit very good extrudability and in particular are well or even very well suited for medical applications. With regard to cost-effective production, these materials moreover have comparatively low material costs. Inexpensive plastics such as PVC, compounds and blends made of PP, PE, TPE-S (SEBS) sometimes have considerable deficits, particularly in terms of temperature resistance. They mostly cannot be employed above 100° C. However, the temperature requirements for disposable endoscopes are significantly lower, so that these materials are particularly suitable for this application due to their low material costs and easy processing. The otherwise commonly required minimum temperature resistance of greater than 133° C. to 137° C., which corresponds to the temperature range during autoclaving of reusable or reprocessable medical devices or components is not necessary in this case, since the processes usually employed as the sterilization processes for disposable medical products are conducted in a temperature range from room temperature to not more than 60° C. An example of a commonly used sterilization method is ethylene oxide fumigation.

The group of inexpensive and medium-priced plastics is usually available in a wide range of elasticity and hardness specifications or can be produced by mixing multiple types of plastics into a poly-blend of desired performance. An advantage over the "expensive" plastics such as FEP, PVDF is that they can be used to produce illumination light guides 30 with virtually identical properties but with different flexibility.

Although the expensive plastics such as FEP, PFA, PVDF can be employed universally and in particular exhibit high permanent temperature resistance, often in combination with high chemical resistance, they cannot but to a very limited extent combined with other plastics or mixed into a polyblend in order to increase flexibility, for example.

All of the plastics mentioned have more or less already been employed for medical products.

In addition to PC and PA, COC is also very well suited as a material for the transparent ferrules, since it is of high optical quality with regard to high transparency and low haze and is in particular used for syringes and pharmaceutical packaging. These materials are in particular also available as biocompatible variants.

With regard to the formation of a flat surface as the proximal or distal end face 43, 53, it is also possible to use casting resins in an advantageous embodiment, in particular low-viscosity casting resins that have particular self-leveling properties.

As an alternative to an extrusion process, the glass fiber bundles or plastic optical fibers may as well be encased in a thin-walled tube or in a shrink tube for their protection. In the case of shrink tubes, advantageously, extremely thin-walled shrink tubes can be used (e.g. PET shrink tube of 6 μm wall thickness). Thin-walled netting tubes made of glass silk or plastic silk are also conceivable.

Most preferably for medical applications, the glass fibers may be made of a Pb-free or heavy metal-free core glass and cladding glass, which is particularly favorable in view of the RoHS and REACH regulation requirements and medical approval. Such glass systems for producing Pb-free or heavy metal-free fibers have been described in documents WO 2013/104748 A1 and DE 102007063463 B4, inter alia, and are known from the present applicant under the name SCHOTT PURAVIS®. Rigid Pb-free or heavy metal-free fiber-optic elements are described in DE 10 2013 208838 B4. Particularly suitable for applications in the field of endoscopy are glass fibers with high NA values, i.e. with acceptance angles $2\alpha>80°$, preferably $2\alpha>100°$, in order to allow for wide illumination on the one hand and optimal incoupling of light by LEDs on the other. Such fibers are known under the names of SCHOTT PURAVIS® GOF85 or GOF120, for example.

Figure 4:
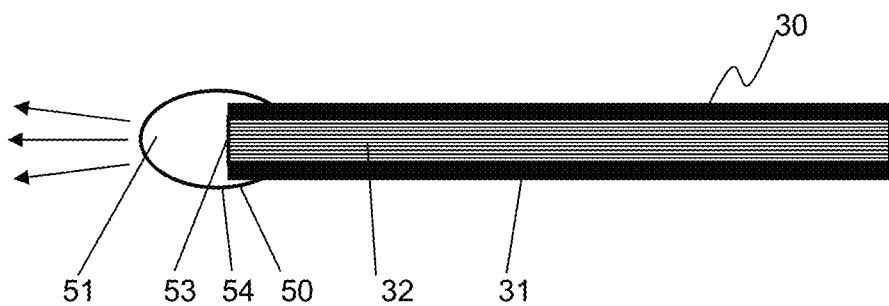
FIG. 4 is a schematic view of an illumination light guide with a distal ferrule molded thereto.

FIG. 4 shows a portion of an alternative approach for an illumination light guide 30 with a distal ferrule 50, which may be similarly implemented for the proximal ferrule 40 as well.

To this end, for example, the fiber bundles are previously extruded, as already described in conjunction with FIG. 3, that is to say the fiber bundle 32 is jacketed with a plastic to form a cable 31, cut to length and then subjected to an injection molding process in which the cable sections are directly overmolded with the transparent plastic to thereby form a ferrule, i.e. distal ferrule 50 in this case. In order to prevent the fiber ends from fanning out, the cable end may have to be grasped at least at two opposite points by semicircular collets and at least partially overmolded. A second injection overmolding process may then be provided to overmold the final ferrule geometry. This makes it possible to form a clear transparent cover for the distal end face 53 on the one hand, optionally with integrated optical functionality in the form of shaped lens elements (optical element 51), and to form a mechanical interface 54 using another plastic which may optionally be a different type of plastic and may even be opaque. The same applies to proximal ferrule 40 which may be provided with a clear transparent cover for the proximal end face 43, optionally with integrally molded optical elements 41, and with a mechanical interface 44 using these method steps.

Figure 5:
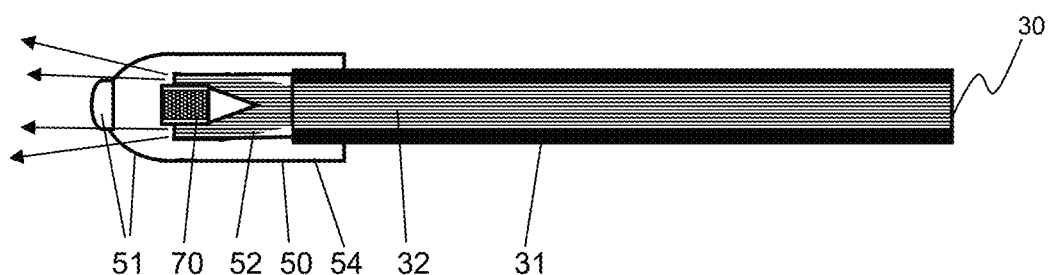
FIG. 5 is a schematic view of an illumination light guide with a distal ferrule and an integrated camera chip.

FIG. 5 shows a variant of the embodiment shown in FIG. 3. Again, distal ferrule 50 is illustrated here by way of example, attached on illumination light guide 30 shown as an extruded cable 31 including the fiber bundle 32. Here, distal ferrule 50 has a central area in which a camera chip 70 (C-MOS chip) may be integrated, for example, in which case the fiber bundle 32 of illumination light guide 30 is routed and arranged around the camera chip 70 in an annular arrangement, an at least partially annular arrangement, or in at least two sub-strands. For this purpose, the receptacle area 52 for the fiber bundle 32 conically widens correspondingly. Also, optical elements 51 may be integrally molded when producing the ferrule, or may be additionally applied in a subsequent adhesive bonding process. In this way, optimal illumination of the tissue area to be examined can be achieved on the one hand, especially shadow-free illumination, and on the other hand this allows to provide imaging optics for the camera chip 70. Furthermore, conceivable is the integration of sensor components such as photodiodes or the like, for detecting particular wavelengths of the light scattered back from the surface to be examined.

Figure 6A:
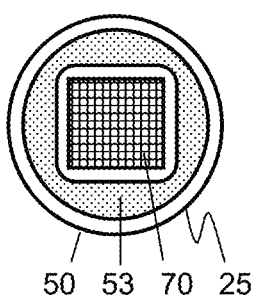
FIGS. 6a to 6c are schematic views of different arrangements of a distal end face with a camera chip.
Figure 6B:
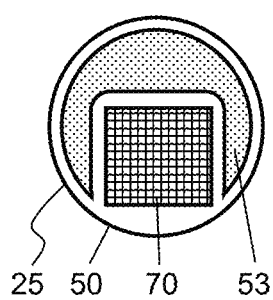
Figure 6C:
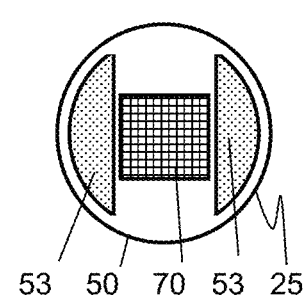

FIGS. 6a to 6c schematically show typical arrangements of the distal end face 53 of the illumination light guide 30 in combination with a camera chip 70, with distal ferrule 50 representing the termination of the shaft 25 of endoscope 1 in these examples. FIG. 6a shows an arrangement in which the camera chip 70 is essentially surrounded by distal end face 53. FIG. 6b shows an essentially U-shaped distal end face 53. FIG. 6c shows an exemplary arrangement in which the camera chip 70 is flanked by a pair of diametrically opposed D-shaped distal end faces 53. Furthermore, 3- or 4-part distal end faces 53 are conceivable, surrounding the camera chip 70 in the form of circular or oval or kidney-shaped exit faces.

The geometric arrangement is predetermined correspondingly by the configuration of the distal ferrule 50. Such ferrules can be produced particularly cost-effectively by injection molding.

Figure 7:
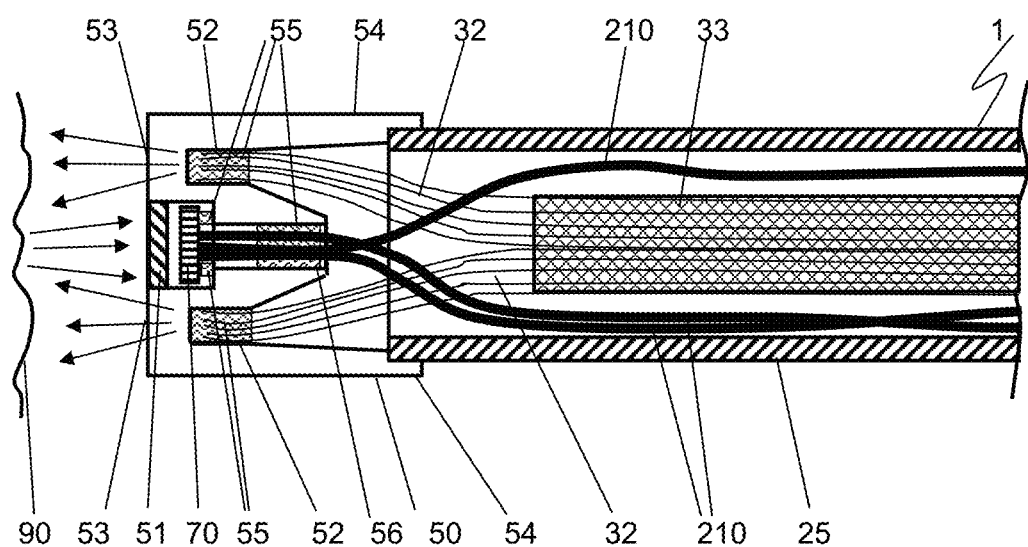

By way of example, FIG. 7 shows a sectional view of a distal ferrule 50 corresponding to the arrangement of distal end face 53 and camera chip 70 as shown in FIG. 6a.

As an example, distal ferrule 50 is shown here as terminating a rigid shaft 25 of the endoscope 1, which shaft may be a stainless steel tube, for example. Distal end face 53 is arranged substantially annularly around the centrally arranged camera chip 70. The light emitted from the distal end face is reflected by a tissue surface 90 to be examined, for example, and is captured by camera chip 70. Camera chip 70 is covered for protection, and the cover may be in the form of an optical element 51, such as a converging lens. An optical element 51 in the form of a multi-lens arrangement is likewise conceivable. Camera chip 70 is electrically connected to electrical lines 210 which are routed through a feedthrough 56 in distal ferrule 50 and into the interior of shaft 25. The fiber bundle 32, here consisting of glass fibers with a high NA (acceptance angle $2\alpha > 100°$), is fanned out to form a ring and is fixed in an annular receptacle area 52 provided about feedthrough 56. This receptacle area 52 has walls that are nearly parallel to one another in order to allow the fibers to be oriented in parallel to one another. Adjoining the receptacle area 52, distal ferrule 50 has conically shaped areas in order to facilitate threading of the fibers. Inside the shaft 25, the fiber bundle 32 is surrounded by a protective sheath 33, which may be in the form of an extruded jacket, a netting tube, or a shrink tube. Given the very small installation space inside shaft 25, it is particularly advantageous if, for example, a thin-walled PET shrink tube is used as the protective sheath. Such shrink tubes have a wall thickness of <10 µm. Distal ferrule 50 may have further mechanical interfaces 54 on its outer contour, for example in the form of a collar, or a diameter step as shown, for joining the distal ferrule 50 to the shaft 25. Moreover, several adhesive bonding areas 55 are provided, on the one hand for fixing the fibers of the fiber bundle 32 and on the other hand for fixing the camera chip 70 or for additionally sealing the feedthrough 56 for the electrical lines 210. With regard to process times and thus costs, it is particularly advantageous if the entire distal ferrule 50 is made of a clear transparent plastic such as PC or PMMA, and if a UV-curing adhesive is used as the adhesive or as a casting resin for the adhesive bonding areas 55. The adhesive or casting resin that is in particular used in the receptacle area 52 for fixing the fibers has an optical refractive index which is substantially matched to that of the core material of the fibers, with a deviation of these refractive indices of at most ±0.1, preferably at most ±0.05, while the refractive index of the ferrule is slightly lower than that of the adhesive.

It will be apparent that such an embodiment with the features as mentioned above is likewise conceivable for a proximal ferrule 40, in which case an LED 60 can be integrated instead of the camera chip 70.

In an embodiment not shown, it is conceivable that the camera chip 70 is mounted on the rear side of distal ferrule 50 and that the distal end face 53 forms a cover. In this way, improved electrical insulation can be achieved without an additional covering element.

Figure 8:
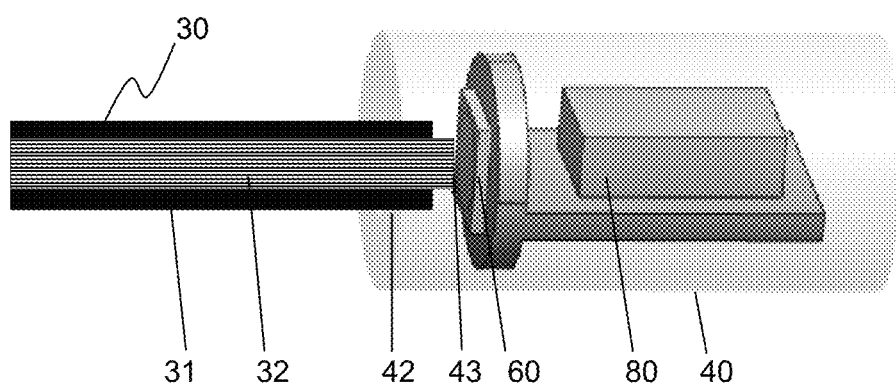
FIG. 8 is a schematic view of an illumination light guide with a proximal sleeve and an illuminating device integrated therein.

FIG. 8 shows a proximal ferrule 40 on the illumination light guide 30, in which an LED 60 along with an LED controller unit 70 is integrated into the proximal ferrule 40. In this way, it is in particular possible to implement a space-saving light source. Here, LED 60 and LED controller unit 70 are integrated in a proximal ferrule 40 that has been produced separately, as described in conjunction with FIG. 3, and the end of fiber bundle 32 is assembled or fixed in a receptacle area 42 formed in proximal ferrule 40. The proximal end face 43 may be provided with a clear transparent cover which may be in the form of a condenser lens or a structure enclosing the LED chip, in order to provide for optimum injection of light into the fiber bundle 32.

Figure 9:
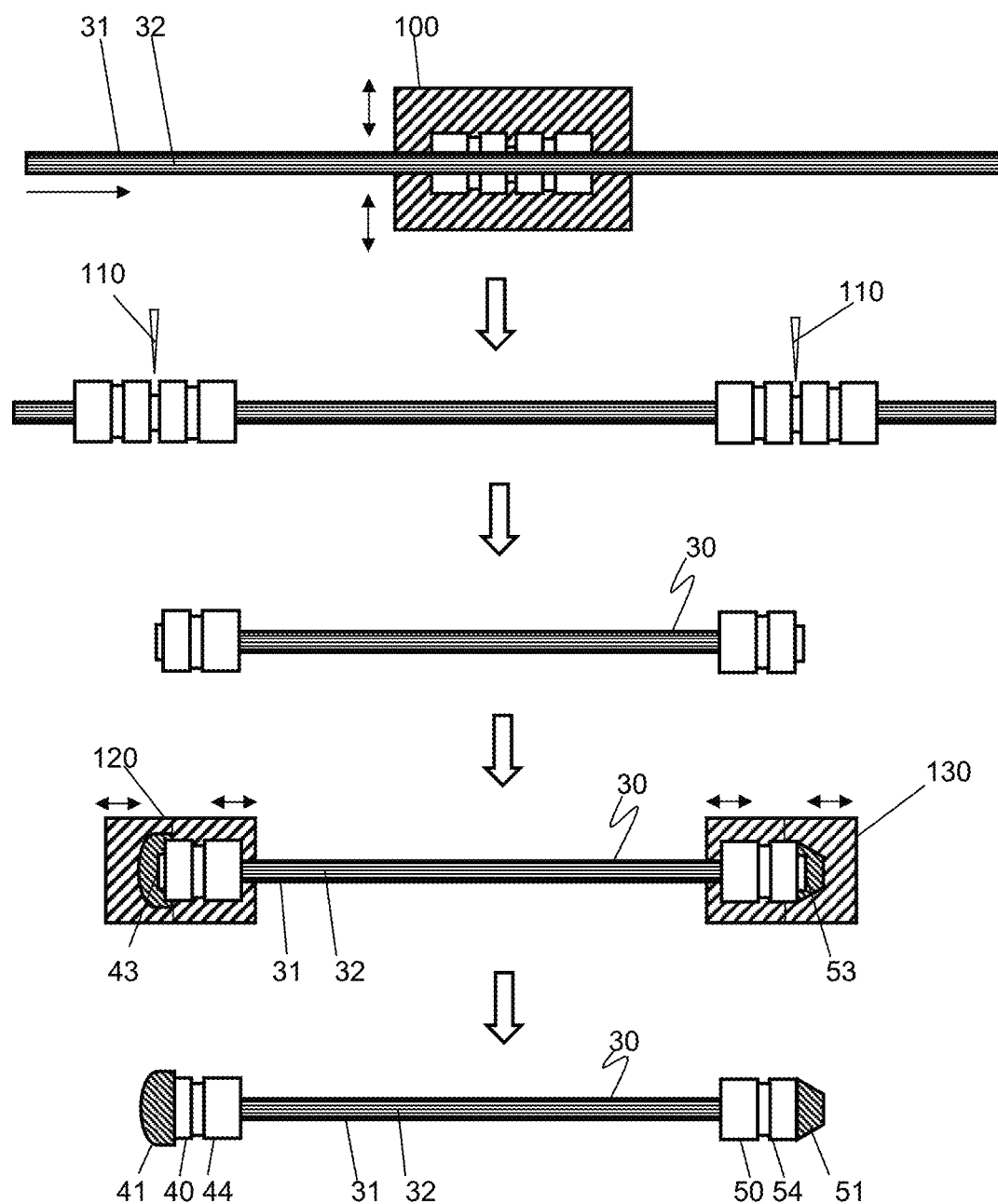
FIG. 9 shows a highly simplified processing sequence of a manufacturing method of an illumination light guide.

Alternatively, as illustrated by a highly simplified process sequence in FIG. 9, a continuous process may be implemented during which a previously extruded cable 31 including the fiber bundle 32 is rewound from an unwinder onto a winder, and the rewinding is stopped at specific intervals and a plastic double ferrule is overmolded thereto by injection molding using a first injection molding tool 100. At this location, a double ferrule is overmolded around the cable 31 in a positively fitting manner without an intermediate layer, which double ferrule is severed together with the cable 31 by severing means 110 in a subsequent cutting process. This is also conceivable directly following the extrusion process, if appropriate measures are provided to adjust or compensate for the processing rates, for example a buffering zone for intermediate storage of the extruded cable. The so terminated cable sections which later correspond to the illumination light guide 30, can then be overmolded in further steps using a second and a third injection molding tool 120, 130, to produce the final ferrule design and in particular using an optically clear transparent plastic, so that simple entry and exit optics (optical elements 41, 51) can be provided on the proximal or distal end faces 43, 53 of the illumination light guide 30 in this way, inter alia. As an alternative, this may also be achieved in an adhesive bonding process, which may also be employed to mount further components such as, e.g., C-MOS cameras or sensors. The advantage hereof is that, on the one hand, firm ferrules can be produced and that in particular the fixation in the tool for the second final overmolding process is made easier by forming respective mechanical interfaces 44, 54. This permits to achieve tight bundle terminations. In this way, high volumes of simple illumination light guides 30 can be obtained very cost-effectively, which is of particular interest for disposable applications and also for consumer applications.

Figure 10:
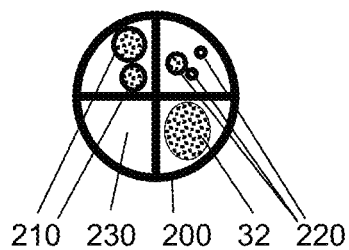
FIG. 10 is a schematic view of a multi-lumen cable for accommodating different components or functionalities.

According to a preferred embodiment, cables known as multi-lumen cables 200 can be produced, as schematically shown in FIG. 10. Such cables may include fiber bundles 32, quartz fibers 220, electrical lines 210, and a fluid passage 230 for carrying media such as gas (e.g. nitrogen), water, medications, and rinsing liquids. The quartz fibers 220 may be used for optical data transfer, for example, or for controlling purposes. Multi-lumen tubes have already been known from literature. A particular advantage thereof lies in the integration of light- and power-carrying components, which provides for high functionality in very restricted space. It can furthermore be envisaged for the cables, inter alia, to be made in a co-extrusion process so as to selectively comprise transparent or opaque segments so that they can moreover fulfil lighting or optical detection tasks.

Another alternative for an inexpensive termination are crimped ferrules as described in DE 10 2004 048741 B3. As an alternative thereto, plastic crimp or latching sleeves may be used, which are prefabricated by an injection molding process and formed with a folding hinge (living hinge) so as to be foldable. Such ferrules are then snap-fitted around the end of the cable section of the extruded cable and can then be filled with optically transparent adhesive in a casting or injection molding process. UV curing adhesives are again advantageous in this case. Besides snap-fitting it may also be envisaged for the ferrules to be fixed on the cable by laser welding or ultrasonic welding.

Another method arises based on the elastic properties of a cable. In this case, it is intended to cut an extruded cable and then to elongate the cable jacket and to fill the resulting cavity with optically clear adhesive or to insert into and fix in the cavity a prefabricated clear transparent plastic part or a glass or plastic light guide rod or fiber rod. Additionally, a fastening feature may be formed by intentionally reshaping the exposed cable sections. Thermoplastic elastomers (TPE) or elastomers such as rubber or silicone are particularly suitable here as the jacket material.

Another alternative for cost-effective termination of light guides may comprise partial heating of a cable filled with gel so that the gel cures there and the cable can then be cut and optionally be reshaped or ferrules can be molded thereto. The cable may also be produced by co-extrusion and may have a transparent section along the axis of the cable, through which the gel can then be selectively cured in sections thereof using UV light. This is another option for implementing a continuous termination process.

LIST OF REFERENCE NUMERALS

1 Endoscope
10 Handpiece
20 Flexible section
25 Shaft
30 Illumination light guide
31 Cable
32 Fiber bundle
33 Protective sheath
40 Proximal ferrule
41 Optical element
42 Receptacle area
43 Proximal end face
44 Mechanical interface
50 Distal ferrule
51 Optical element
52 Receptacle area
53 Distal end face
54 Mechanical interface
55 Adhesive bonding area
56 Feedthrough
60 LED
70 Camera chip
80 LED controller unit
90 Tissue surface
100 $1^{st}$ injection molding tool
110 Severing means
120 $2^{nd}$ injection molding tool
130 $3^{rd}$ injection molding tool
200 Multi-lumen cable
210 Electrical lines
220 Quartz fibers
230 Fluid passage

The invention claimed is:

1. A device for being introduced into the human or animal body or for in-vitro examination of human or animal blood samples or other body cells, comprising:
   a guide for transmitting electromagnetic radiation, wherein the guide has a proximal end face for incoupling or outcoupling of electromagnetic radiation and has a distal end face for incoupling or outcoupling of electromagnetic radiation,
   wherein at least one of the proximal end face and the distal end face are elements that are made of a plastic that is at least partially a transparent plastic or are overmolded with a transparent plastic, wherein the transparent plastic is biocompatible and/or non-cytotoxic to human or animal cell cultures over exposure durations of less than one day and is selected from the group consisting of cyclo-olefin copolymers, polycarbonates, polyethylene terephthalates, perfluoroalkoxy polymers, polyvinylidene fluorides, polymethyl methacrylates, polymethyl methacrylimides, acrylic-styrene-acrylonitrile copolymers, or room temperature crosslinking silicone, hot crosslinking liquid silicones, epoxy casting resins or adhesives, thermally or UV crosslinking acrylate casting resins, polyurethane casting resins, polyester casting resins, and combinations thereof.

2. The device of claim 1, wherein at least one of the proximal end face and the distal end face of the guide further comprises a mechanical interface, wherein the mechanical interface is a ferrule contour made of a ferrule plastic, and
wherein the ferrule plastic differs from the transparent plastic at least partially with respect to its material, transparency, and/or color.

3. The device of claim 1, wherein the transparent plastic has a surface roughness $R_a$ of ≤1.0 μm.

4. The device of claim 1, wherein the transparent plastic has a refractive index which substantially matches that of a core material of fibers or fiber components used in the guide, with a deviation thereto of not more than ±0.1.

5. The device of claim 1, wherein the guide comprises at least one of:
a fiber bundle consisting of glass optical fibers, quartz optical fibers, or plastic optical fibers; and
individual fibers made of glass, quartz, or plastic, wherein the individual fibers are enclosed at least partially or in sections thereof by any of a jacket, tube, shrink tube, or netting tube, or are protected by a shaft of the endoscope.

6. The device of claim 5, wherein the jacket is made of a jacket plastic and is an extruded cable.

7. The device of claim 6, wherein the jacket plastic is a plastic that is translucent, opaque, or colored at least partially.

8. The device of claim 5, wherein the guide consists of the fiber bundle, and the fiber bundle is flexible or semi-flexible.

9. The device of claim 1, wherein the guide consists of drawn fiber rods or pressed fiber rods and is a rigid guide.

10. The device of claim 5, wherein the fibers of the fiber bundle and/or the individual fibers are made of a Pb-free or heavy metal-free core glass and cladding glass.

11. The device of claim 5, wherein the fibers of the fiber bundle and/or the individual fibers are made of a glass system which has an acceptance angle 2α of greater than 80° for the light to be carried.

12. The device of claim 1, wherein the distal end face and/or the proximal end face with the mechanical interface comprise a ferrule that is formed separately and is fixed on a fiber bundle end or fiber rod end of the guide with an adhesive or casting resin,
wherein the adhesive is a thermally curing or UV light curing adhesive which has an optical refractive index substantially matching that of the core material of the fibers or fiber components used in the guide, with a deviation thereto of not more than ±0.1, and
wherein the refractive index of the ferrule is lower than that of the adhesive or casting resin.

13. The device of claim 12, wherein the ferrule comprises receptacle areas for accommodating a fiber bundle,
wherein the receptacle areas comprise a conical portion transitioning into a portion that has substantially parallel side walls,
wherein the ferrule furthermore has seats for electronic components, and
wherein the receptacle areas at least partially surround the seats.

14. A process of making the device of claim 2, comprising the steps of:
forming the distal and/or proximal end faces with the mechanical interface in the form of a ferrule by injection molding on cable sections previously cut to length so that the cable has a cable end;
fixing the cable end at least at two opposite points by tools adapted to the outer contour of the cable;
overmolding the cable end at least partially or in sections thereof with a first plastic;
molding a geometry of the ferrule to the cable end with a second plastic; and
optionally, molding the distal and/or proximal end faces with the transparent plastic in any one of said forming, fixing, overmolding, and molding steps.

15. The device of claim 1, wherein the proximal end face and/or the distal end face of the guide further comprises an active electronic component that is selected from the group of an LED, a laser diode, a sensor, a camera chip, and combinations thereof, wherein the active electronic component is integrated into the overmolded ferrules or can be fitted thereto with a snap-in connection.

16. The device of claim 15, further comprising additional glass or plastic components on the proximal end face and/or the distal end face for covering the active electronic components.

17. The device of claim 1, wherein the proximal end face and/or the distal end face is an optical element to achieve specific beam shaping.

18. The device of claim 6, wherein the extruded cable is a hybrid cable.

19. The device of claim 18, wherein the hybrid cable is a multi-lumen cable that separately routes fiber bundles, individual quartz fibers, and media in the form of gases or liquids into at least one of a fluid passage and an electrical lines.

20. The device according to claim 19, wherein the multi-lumen cable defines a flexible portion of the endoscope; or
wherein the multi-lumen cable is made of a plastic that is rigid at room temperature and defines a rigid shaft of the endoscope.

21. The device of claim 18, wherein the hybrid cable is produced by a co-extrusion process so as to be transparent or opaque in segments thereof.

22. A process for making the device of claim 1, comprising the steps of:
in a continuous process, overmolding a double contour ferrule on a previously extruded cable at specific intervals corresponding to a length of a mechanical interface;
severing the cable at the length of the mechanical interface to produce a cable section;
molding the proximal end face and/or the distal end face to the cable section in an injection molding process using clear transparent plastic.

23. The process of claim 22, wherein the cable section has a fiber bundle enclosed therein, and the fiber bundle has been offset in from an edge of the cable section, the method further comprising the step of:

filling the space between the fiber bundle end and the edge of the cable section with a transparent self-leveling plastic.

24. The process of claim 23, wherein the cable section has a fiber bundle enclosed therein, and the fiber bundle has been offset in from an edge of the cable section, the method further comprising the step of:

filling the space between the fiber bundle end and the edge of the cable section with a transparent self-leveling plastic with an optically transparent plastic or a prefabricated clear transparent plastic part; or inserting or fixing a glass or plastic light guide rod or fiber rod into the space between the fiber bundle end and the edge of the cable section.

25. The device of claim 1, wherein the guide is at least one of an illumination light guide and an image guide.

26. The device of claim 2, wherein the ferrule plastic is injection molded plastic.

27. The device of claim 1, wherein the device is an endoscope.

\* \* \* \* \*